United States Patent [19]
Takata et al.

[11] Patent Number: 4,629,464

[45] Date of Patent: Dec. 16, 1986

[54] POROUS HYDROXYAPATITE MATERIAL FOR ARTIFICIAL BONE SUBSTITUTE

[75] Inventors: Susumu Takata; Shoichi Wakabayashi, both of Tokyo; Hiroyasu Noma, Mitaka; Tatsuya Wakatsuki, Tokyo, all of Japan

[73] Assignee: TDK Corporation, Tokyo, Japan

[21] Appl. No.: 770,722

[22] Filed: Aug. 29, 1985

[30] Foreign Application Priority Data

Sep. 25, 1984 [JP] Japan .................................. 59-200129
Sep. 25, 1984 [JP] Japan .................................. 59-200130
Sep. 25, 1984 [JP] Japan .................................. 59-200131

[51] Int. Cl.$^4$ ............................................ C07C 61/06
[52] U.S. Cl. ..................................................... 623/16
[58] Field of Search ............................ 623/16; 106/35; 433/201

[56] References Cited

U.S. PATENT DOCUMENTS 3,423,829  1/1969  Halpern et al. ...................... 106/35
3,913,229  10/1975  Driskell ................................ 106/35
3,919,139  11/1975  Keegan ................................. 106/35
4,222,128  9/1980  Tomonasa ............................ 623/16

Primary Examiner—Gregory E. McNeill

Attorney, Agent, or Firm—Wyatt, Gerber Shoup, Scobey and Badie

[57] ABSTRACT

The sintered microporous hydroxyapatite material of the invention is useful as an artificial bone substitute material either in a granular and slurried from in a physiological saline solution used as a filling material for lost portions or cavities of bones or in a form of a shaped prosthetic bone substitute member. The inventive material is characteristic in the open pore structure of micropores with a pore diameter distribution in the range from 0.01 to 0.10 mm and a porosity in the range from 20 to 50%. When the material is used in the form of a granular bone filling, the particle diameter thereof should be in the range from 0.1 to 2.0 mm. When the material is used as the prosthetic bone substitute member, the shaped body should be formed of the matrix of the inventive microporous material and pores with a pore diameter distribution in the range from 0.2 to 2.0 mm. When an increased bending strength is desired, the prosthetic member should preferably have a core-and-crust structure of which the matrix of the core portion and the crust layer having a thickness of 0.1 to 2 mm are formed of the inventive microporous material, the core portion being formed of the matrix and pores of 0.2 to 2.0 mm diameter distribution throughout the matrix.

7 Claims, 2 Drawing Figures

POROUS HYDROXYAPATITE MATERIAL FOR ARTIFICIAL BONE SUBSTITUTE

BACKGROUND OF THE INVENTION

The present invention relates to a novel porous hydroxyapatite material suitable for use as an artificial bone substitute or, more particularly, to a porous hydroxyapatite material usable as a granular filling in a cavity or a lost portion of bones and also as a sintered body for prosthesis of bones in the fields of dentistry, stomatoplasty, orthopedics and the like.

One of the problems in the dental treatment is absorption of the alveolar bone after tooth extraction to cause instability in the fixation of an artificial tooth necessitating a filling material. In the treatment of stomatoplasty and orthopedics, it is a common practice to undertake prosthesis of bone lost in a traffic accident or as a result of bone tumor with a material for bone substitute. Although autografting of bone, i.e. implantation of a piece of bone taken from a part of a patient's body to the lost portion or cavity in the bone of the same patient, is a preferable way from the physiological standpoint, a very serious physical and psychological load is unavoidable on the patient in the autografting of bone because the bone piece used for autografting must be taken from an unaffected bone tissue of the patient himself. Needless to say, no bone piece for autografting having a sufficiently large volume can be obtained to cover a large lost portion of the bone. Accordingly, intensive investigations have been and are being undertaken to develop an artificial material for bone substitute as a filling of a bone cavity or as a prosthetic member of a bone. Such an artificial bone substitute material must satisfy several requirements including, for example, a high degree of safety or absence of toxicity, sufficient mechanical strength, good affinity to the living body tissue in which the material is embedded or implanted to form a firm bond therebetween, and others. Further, it is sometimes desirable that the implanted artificial material is spontaneously absorbed and disappears in the lapse of time to be replaced with a neogenetic bone tissue. In this regard, prosthetic members made of a metal such as titanium, stainless steel, aluminum and the like are not always satisfactory due to the lack of metabolizability despite their high mechanical strengths. When a prosthetic member made of these unmetabolizable materials is used, it must be removed by operation after complete cure or must be left remaining in the patient's body lastingly though with an apprehension of some adverse influences thereby as a foreign body.

A class of promising artificial bone substitute materials recently developed in view of these requirements include tricalcium phosphate, hydroxyapatite, specific calcium phosphate of an apatite-like crystalline structure and the like in a sintered form and extensive investigations are now under way to develop artificial bones, artificial articulations, artificial dental roots and the like using these materials.

It is a desirable condition that the artificial bones, artificial dental roots and the like substitute bodies have a porous structure in order to facilitate formation of a firm bond between the living body tissue and the substitute body implanted therein by the proliferating growth of the living body tissue into the pores of the porous substitute body. In this regard, a proposal has been made in Japanese Patent Kokai Nos. 56-149389 and 57-7856 for the use of a porous sintered body of calcium phosphate in which the pores have diameters in the range of about 0.03 to 1.2 mm. This porous sintered body of calcium phosphate is, however, defective as an artificial bone substitute due to the brittleness and insufficient mechanical strength. The material is also not quite satisfactory in respect of the absorptivity in the living body and replaceability with a neogenetic bone tissue due to the dense texture of the base material.

In respect of a granular filling material used in a cavity of bones, a proposal is made in Japanese Patent Kokai No. 56-54841 of a powdery product of calcium phosphate having an apatite-like crystalline structure with a crystallite diameter in the range from 5 nm to 10 $\mu$m which is used for filling a cavity or a lost portion of a bone in the form of a slurry with addition of a physiological saline solution. A problem in this powdery material is that, because the particles thereof are so finely divided, particles sometimes adhere to the traumatic surface of the skin to cause difficulties in suture of the trauma.

SUMMARY OF THE INVENTION

It is therefore a primary object of the present invention to provide a bone substitute material free from the above described problems and disadvantages in the prior art materials.

Another object of the invention is to provide a hydroxyapatite-based bone substitute material which is usable either as a granular filling material for bone cavity or as a prosthetic member in the form of a sintered body.

Thus, the hydroxyapatite-based bone substitute material of the invention is a sintered microporous hydroxyapatite body of an open pore structure having a porosity in the range from 20% to 50%, of which the micropores have a distribution of diameters in the range from 0.01 to 0.1 mm.

When the above defined microporous hydroxyapatite body is to be used as a filling in a bone cavity, it is in a granular form of which the granules have a distribution of diameters in the range from 0.1 to 2.0 mm and the granular form may be prepared as a slurry with admixture of a physiological saline solution.

When the above defined porous hydroxyapatite body is to be used as a prosthetic member of bones, on the other hand, the member is formed of a matrix phase of the above defined sintered microporous hydroxyapatite body having a distribution of the micropore diameters in the range from 0.01 to 0.1 mm or, preferably, from 0.02 to 0.1 mm and a porosity of 20 to 50% and the matrix phase is further provided with pores having diameters in the range from 0.2 to 2 mm distributed throughout.

It is optional that, when the above described prosthetic member of the porous hydroxyapatite body having coexisting classes of pores relative to the pore diameter is desired to have a further increased mechanical strength as a whole, the member is further provided on at least a part thereof with a crust layer of sintered hydroxyapatite of open pore structure having a thickness of 0.1 to 2 mm and a micropore diameter in the range from 0.01 to 0.1 mm or, preferably, from 0.02 to 0.1 mm so that the prosthetic member has a core-and-crust structure.

DETAILED DESCRIPTION OF THE PREFERRED EMBODIMENTS

Figure 1:
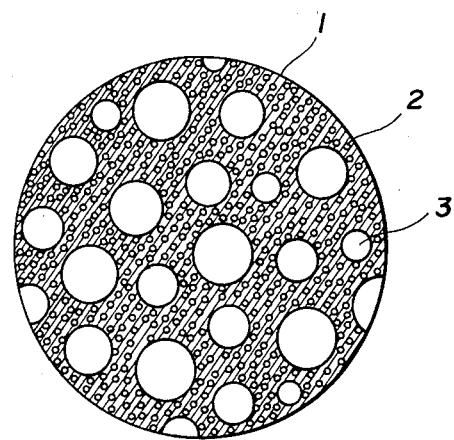
FIG. 1 is a schematic illustration of a cross sectional view of a prosthetic bone member of the invention having two classes of pores relative to the pore diameter.

The microporous hydroxyapatite body as mentioned above can be prepared, taking the granular form suitable for filling use as a product form, for example, by admixing 100 parts by weight of a powdery hydroxyapatite having a particle size distribution as fine as possible or in the range from 0.1 to 10 $\mu$m with from 25 to 100 parts by weight of a thermally decomposable powdery material having a particle diameter in the range from 0.01 to 0.1 mm and granulating the powdery blend into granules having a particle diameter in the range from 0.1 to 3 mm by a known method, optionally, with admixture of a suitable binder such as an aqueous solution of polyvinyl alcohol followed by calcination and sintering of the granules at a temperature in the range from 900° to 1400° C.

The starting powdery hydroxyapatite used in this preparation can be either a synthetic hydroxyapatite prepared by a wet process or dry process or a so-called living body hydroxyapatite obtained from bones and teeth of various kinds of vertebrate animals. Although it is desirable from the standpoint of product quality that the powdery hydroxyapatite has a particle size distribution as fine as possible, it is usually practical that the average particle diameter thereof is in the range from 0.1 to 10 $\mu$m in view of the capability of the pulverizing machine and particle size classifier and facility in handling of a powdery material divided in an adequate fineness.

The thermally decomposable powdery material blended with the hydroxyapatite powder serves to leave an open pore structure having a desired micropore diameter in the sintered texture of the hydroxyapatite particles so that the powdery material should essentially have an average particle diameter in the range from 0.01 to 0.1 mm. In order to satisfy the other essential requirement of the sintered microporous hydroxyapatite material relative to the porosity in the range from 20 to 50%, the blend of the powdery hydroxyapatite and the thermally decomposable powdery material should preferably be prepared of 100 parts by weight of the former and from 25 to 100 parts by weight of the latter. When the amount of the thermally decomposable powdery material is smaller than above, the resultant sintered microporous hydroxyapatite body would have a microporosity of less than 20% so that the development of the open pore structure may be insufficient. When the amount thereof is too large, on the other hand, the microporosity of the sintered body would be excessively large with unavoidable mechanical fragility of the structure. The thermally decomposable powdery material suitably used in this purpose is exemplified by crystalline cellulose though not particularly limited thereto.

Blending of the powders of the hydroxyapatite and the thermally decomposable material, e.g. crystalline cellulose, may be performed in several different ways known in the conventional powder technology. For example, the simplest way is the direct dry blending of the powders in a suitable powder blending machine such as a V-mixer. Alternatively, it is optional that the powdery hydroxyapatite alone is granulated in avance into granules having a particle diameter in the range from 0.02 to 0.2 mm and the granules are then blended with the crystalline cellulose. Further alternatively, the powder of crystalline cellulose is moistened with water or other solvent and then sprinkled with the powdery hydroxyapatite to be covered therewith. The powdery blend thus prepared is granulated in a known granulator with optional admixture of a binder such as an aqueous solution of polyvinyl alcohol into granules having a desired particle size distribution and calcined and sintered at a temperature in the range from 900° to 1400° C. The particle diameter of the granules before calcination and sintering should be determined taking the shrinkage of the particles during heating into account so as to give a particle diameter in the range from 0.1 to 2 mm after calcination and sintering. The length of time for the calcination and sintering is usually in the range from 0.5 to 3 hours to achieve complete thermal decomposition and dissipation of the thermally decomposable powdery material.

The above mentioned particle diameter is essential in the sintered microporous hydroxyapatite in the granular form for filling use according to the invention. When the granules are finer than above, some inconveniences are caused in the filling use thereof due to the adhering particles on the traumatic surface which disturb suturing of the trauma even when the granules are used in the form of a slurry or paste with admixture of a physiological saline solution. When the granules are coarser than above, on the other hand, no slurry or paste suitable for the filling use can be prepared by the admixture of a physiological saline solution. A slurry or paste of the microporous granules can be obtained by mixing the granules and a physiological saline solution in a weight ratio in the range from 2:1 to 1:2.

The above described porous artificial bone filling is a sintered granular hydroxyapatite material having an open pore structure of a specific pore diameter distribution and is very advantageous when used to fill up a bone cavity or lost part of a bone by virtue of the unique combination of the parameters including the particle diameter, which is in the range from 0.1 to 2.0 mm, pore diameter, which is in the range from 0.01 to 0.1 mm, and porosity, which is in the range from 20 to 50%, due to the easiness of forming a strong bond with the living body tissue, growing intrusion of the osteoclast cells having a diameter of 50 to 100 $\mu$m into the pores and dissolution and absorption of the filling by the activity of the osteoclast cells to be completely replaced with the neogenetic bone by means of the osteoclast cells.

In addition to the above described application as an artificial bone filling in the form of granules, the porous sintered hydroxyapatite body of the invention can be a porous shaped body which is useful as a bone substitute member in the prosthesis. It has been found that the prosthetic bone substitute member according to the invention is particularly useful when it has a structure formed of a matrix, which in itself is porous having micropores of a diameter in the range from 0.01 to 0.1 mm or, preferably, from 0.02 to 0.1 mm to give a porosity of 20 to 50%, and larger pores distributed in the matrix having a diameter in the range from 0.2 to 2.0 mm. In other words, the prosthetic bone substitute member according to the invention has pores capable of being classified into two classes relative to the pore diameter, a first class of the pores having a pore diameter in the range from 0.01 to 0.1 mm and the second class of the pores having a pore diameter in the range from 0.2 to 2.0 mm.

Such a prosthetic bone substitute member of the invention can be prepared according to the procedure, for example, described below. The starting material is a powder of hydroxyapatite having a particle diameter in the range from 0.1 to 10 $\mu$m, which may be either a wet-process or dry-process synthetic hydroxyapatite or a living-body hydroxyapatite recovered from bones or teeth of vertebrate animals. Such a finely divided hydroxyapatite powder taken in an amount of 100 parts by weight is uniformly blended with from 10 to 40 parts by weight of a first thermally decomposable powdery material having a particle diameter in the range from 0.01 to 0.1 mm and from 10 to 40 parts by weight of a second thermally decomposable powdery or granular material having a particle diameter in the range from 0.2 to 2.0 mm and the powdery blend is shaped into a desired form of a bone substitute member followed by calcination and sintering at a temperature in the range from 900° to 1400° C. If desired, sintering may be performed by use of a hot press under a pressure of 300 to 1000 kg/cm$^2$.

It is essential that two classes of the thermally decomposable materials should be used each in the above specified amount in order that the sintered body may have pores classified into two classes relative to the pore diameter. The above specified amount of each class of the thermally decomposable materials is essential in order that the sintered body may have an open cell structure and still retain high mechanical strengths useful as a bone substitute. The thermally decomposable material is preferably a crystalline cellulose though not limited thereto.

The method for blending the powdery hydroxyapatite and the crystalline cellulose powders is not particularly limitative including any conventional methods capable of giving uniformity of the powdery blend. For example, the hydroxyapatite powder and two classes of the crystalline cellulose powders may be directly blended in a suitable blending machine. Alternatively, the hydroxyapatite powder alone is first granulated into granules having a diameter of 0.02 to 0.2 mm followed by blending with the crystalline cellulose powders. Further alternatively, the crystalline cellulose powders are moistened with water or other solvents and the hydroxyapatite powder is dusted on the moistened particles of the crystalline cellulose. The powdery blend is, after admixture of a binder such as polyvinyl alcohol in an aqueous solution according to need, shaped by compression molding into a desired form of a bone substitute and sintered at a temperature in the range from 900° to 1400° C., usually, for 0.5 to 3 hours.

It is further optional that a powdery blend prepared of 100 parts by weight of the hydroxyapatite powder and from 10 to 40 parts by weight of the first, i.e. finer, powder of the thermally decomposable substance having a particle diameter of 0.01 to 0.1 mm is first granulated into granules and then the granules are blended with 10 to 40 parts by weight of the second, i.e. coarser, powder of the thermally decomposable substance having a particle diameter of 0.2 to 2 mm, if necessary, together with a binder followed by shaping into a desired form of a bone substitute to be sintered.

Although the microporous matrix of the inventive bone substitute member has a bending strength of 140 to 150 kg/cm$^2$ in itself, the thus prepared prosthetic artificial bone substitute member as a whole usually has a bending strength of 80 to 130 kg/cm$^2$ with an overall porosity of 30 to 40% and water absorptivity of 20 to 40% by weight.

Hereinafter the pore structure of the thus prepared artificial bone substitute member is explained with reference to the accompanying drawing. FIG. 1 of the accompanying drawing is an enlarged schematic illustration of a partial cross section of the inventive artificial bone substitute member, in which the structure of the member is formed of the matrix 1, which is a microporous sintered material of hydroxyapatite with uniformly distributed micropores 2 having a pore diameter of 0.01 to 0.1 mm, and larger pores 3 having a pore diameter of 0.2 to 2 mm uniformly distributed throughout the matrix 1.

The unique pore diameter distribution in the inventive bone substitute member permits growing intrusion of the capillaries having a diameter of 7 to 10 $\mu$m into the pores to facilitate formation of bone tissues by the osteoblast cells and spontaneous absorption of the hydroxyapatite by the appearance of the osteoclast-like multinuclear giant cells so that the inventive bone substitute member is very useful for prosthesis in orthopedics and stomatoplasty.

The above described artificial bone substitute member has a sufficiently high mechanical strength or overall bending strength of 80 to 130 kg/cm$^2$ suitable for most purposes but it is sometimes desirable to further increase the overall bending strength of the member with an object to replace the high-strength prosthetic member conventionally made of stainless steel or other metals. In this regard, the inventors have further continued investigations and arrived at an improvement that a bone substitute member having a higher bending strength can be prepared by providing the above described bone substitute member having a binary pore diameter distribution as a core on at least a part of the surface thereof with a crust layer having a thickness of 0.1 to 2 mm formed of a microporous sintered hydroxyapatite body in which the pores have a diameter in the range from 0.01 to 0.1 mm. By this means, it is easy to obtain a bone substitute member having an overall bending strength of 160 kg/cm$^2$ or larger. Despite the relatively dense crust layer formed on the core, such a bone substitute member of core-and-crust structure is physiologically quite satisfactory when used in prosthesis.

The above mentioned bone substitute member of composite core-and-crust structure can be prepared by first shaping a powdery blend composed of 100 parts by weight of a fine hydroxyapatite powder having an average particle diameter of 0.1 to 10 $\mu$m, 10 to 40 parts by weight of a first, i.e. finer, powder of a thermally decomposable substance having an average particle diameter of 0.01 to 0.1 mm and 10 to 40 parts by weight of a second, i.e. coarser, powder of a thermally decomposable substance, for example, by compression molding into a form having dimensions approximately as desired and then coating the thus shaped form with a powdery mixture, in an aqueous slurry, if neccessary, of 100 parts by weight of the same hydroxyapatite powder and 10 to 40 parts by weight of the finer powder of the thermally decomposable substance to form a crust layer of a desired thickness followed by calcining and sintering of the thus prepared composite green body at a temperature in the range from 900° to 1400° C.

Alternatively, a two-step procedure described below is also suitable. Thus, a powdery blend of 100 parts by weight of the hydroxyapatite powder and 10 to 40 parts by weight of the finer powder of the thermally decomposable substance is first sintered into a microporous sintered body having pores of 0.01 to 0.1 mm diameter and a bending strength of at least 100 kg/cm$^2$ and this sintered body is crushed into granules of 0.05 to 0.2 mm diameter. Then, the granules are blended with 10 to 40 parts by weight of the coarser powder of the thermally decomposable substance and this blend is shaped into the form of the core which is coated with a powdery blend of the hydroxyapatite powder and the finer powder of the thermally decomposable substance in a desired thickness into a composite core-and-crust structure to be subjected to calcination and sintering.

Figure 2:
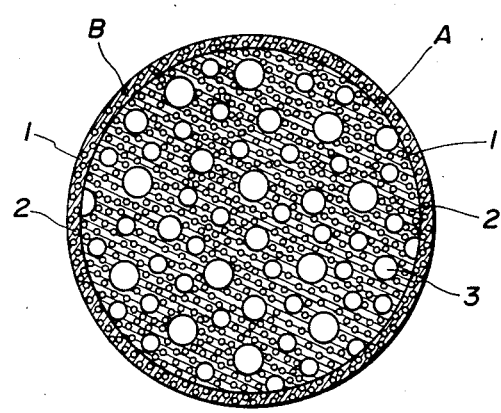
FIG. 2 is a schematic illustration of a cross sectional view of a prosthetic bone member of the invention having a core-and-crust structure.

The core-and-crust structure of the composite bone substitute member is schematically illustrated in FIG. 2 by an enlarged cross section. The member is formed of the core A and crust B and the core A in turn has a binary porous structure formed of the microporous matrix 1 containing the micropores 2 having a pore diameter of 0.01 to 0.1 mm and larger pores 3 having a pore diameter of 0.2 to 2 mm distributed throughout the matrix 1 while the crust B has the same microporous structure as the matrix 1 of the core A containing the micropores 2 having a pore diameter of 0.01 to 0.1 mm.

In the following, examples are given to illustrate the sintered porous hydroxyapatite materials of the invention either in the form of a bone filling or in the form of an artificial prosthetic bone member in more detail.

EXAMPLE 1

Hydroxyapatite synthesized by the wet process was calcined at 900° C. for 1 hour and pulverized in a ball mill into a fine powder having an average particle diameter of about 0.5 μm. The hydroxyapatite powder was uniformly blended with 2% by weight of polyvinyl alcohol in a 13% by weight aqueous solution as a binder and 50% by weight of a crystalline cellulose powder having an average particle diameter of 0.05 mm. The powdery blend was granulated into granules having a diameter in the range from 0.5 to 3.0 mm and the granules were sintered at 1350° C. for 1 hour. The thus obtained sintered granules of hydroxyapatite had an open pore structure with an average pore diameter of 0.05 mm and a porosity of 26%.

When the above obtained granular sintered body of hydroxyapatite was mixed with an equal amount by weight of a physiological saline solution, a slurried mixture was obtained which was usable as a bone filling. Thus, the slurried filling material was used in the operation for filling up a lost portion of the mandible bones of rabbits to find that suturing could be performed very easily with no filling particles adhering to the traumatic surface on the skin.

Microscopic inspection of the bone tissue of the thus operated rabbit mandibles was undertaken after 12 weeks and 24 weeks from the operation to obtain following results.

After 12 weeks, the neogenetic bone tissue formed in the interstices of the hydroxyapatite granules had a clearly recognizable lamellated structure with increase in the thickness and density. Appearance of osteoclast cells was partly noted to exhibit absorption of the neogenetic bone of the lamellated structure formed in contact with the hydroxyapatite granules indicating active progress of the mechanism of the bone reformation. In addition, decrease was noted in the volume proportion occupied by the intervening hydroxyapatite granules.

On the other hand, the condition of the periosteum of the matrix bone was nearly normal while a lamellated structure was found in the neogenetic bones on the outer side of the matrix bone with a single-layer arrangement of osteoblast cells along the periphery thereof.

After 24 weeks, the neogenetic bones formed in the interstices of the hydroxyapatite granules had increased thickness and density to give an appearance that the hydroxyapatite granules were distributed among the neogenetic bones. The lacunae in the neogenetic bone were arranged with increased regularity and the lamellae were oriented in the direction of the longitudinal axis of the mandible bone. Further, formation of an enlarged haversian canal and bone marrow was noted while the hydroxyapatite granules had disappeared by being replaced with a network-like or irregular bone tissue formed instead.

COMPARATIVE EXAMPLE 1

For comparison, the same test as above with rabbits as the test animals was undertaken using a slurry of a porous hydroxyapatite powder having a particle diameter of 5 to 10 μm, which was prepared by calcination and pulverization of the wet-process hydroxyapatite in the same manner as in Example 1 but without granulation and sintering, in equal amount by weight of a physiological saline solution.

The results were that difficulties were encountered in suturing due to the adherence of the slurried particles to the traumatic surface on the skin. The microscopic inspection of the bone tissue indicated following changes after 12 and 24 weeks from the operation.

After 12 weeks from the operation, the condition of the periosteum on the matrix bone was about the same as in Example 1 to show a thick layer of a lamellar bone on the surface. Namely, the neogenetic bone tissue filling the interstices of the granules had increased thickness and density. The neogenetic bone tissue was found to be directly bonded with the hydroxyapatite particles at many points but no change was noted in the outer configuration of the granules.

After 24 weeks, the interstices of the granules were found to be filled with the neogenetic bone tissue although some of the hydroxyapatite granules were found to be surrounded by the fibrous connective tissue. When comparison is made with Example 1, the amount of the fibrous connective tissue was larger but the activity of the bone tissue was lower with consequently slower progress of the mechanism of bone re-formation in the portions in direct bonding with the hydroxyapatite granules.

EXAMPLE 2

Hydroxyapatite synthesized by the wet process was calcined at 900° C. for 1 hour and then pulverized in a ball mill into a powder having an average particle diameter of 0.5 μm. The powder was admixed with 2% by weight of polyvinyl alcohol in an aqueous solution as a binder and granulated into granules having a diameter in the range from 0.05 to 0.10 mm.

The thus obtained granules in an amount of 100 parts by weight were uniformly blended with each 15 parts by weight of a finer and a coarser crystalline cellulose powders having an average particle diameter of 0.08 mm and 0.2 mm, respectively, and the powdery blend was shaped by compression molding under a molding pressure of 500 kg/cm² into a form which was subjected to sintering at 1350° C. for 1 hour.

The thus obtained sintered body of hydroxyapatite of an open pore structure had a porosity of 32% in which the pore diameter distribution had two maxima at 0.05 to 0.08 mm and at about 0.2 mm. The bending strength of this porous sintered body was 145.5 kg/cm² in the matrix portion, i.e. the portion containing only the finer pores of 0.05 to 0.08 mm in the average diameter, while the bending strength of the body as a whole was 102.8 kg/cm².

The thus obtained sintered body was cut into small pieces each having dimentions of 3 mm by 4 mm by 6 mm and the pieces were, after sterilization in a conventional manner, implanted in the mandible bones of 5 rabbits each having a body weight of 2.5 to 3.0 kg. The dissective inspection of the rabbits raised for 8 weeks after the operation indicated partial absorption of the sintered body of hydroxyapatite and complete adhesion of the neogenetic bone to the surface of the sintered body. This result supports the clinical utilizability of the artificial bone substitute member according to the invention as a prosthetic material for lost parts of maxillary bones.

For comparison, a similar implantation test with rabbits was undertaken using pieces of a sintered body of hydroxyapatite prepared in the same manner as described above in which the finer pores had a diameter distribution in the range from 1 to 5 $\mu$m. The result was that little absorption of the sintered body was found.

EXAMPLE 3

The same wet-process hydroxyapatite as used in Example 2 was calcined at 900° C. for 1 hour and pulverized into a powder having an average particle diameter of 0.5 $\mu$m. A powdery mixture of 100 parts by weight of the above prepared hydroxyapatite powder with 2 parts by weight of polyvinyl alcohol as an aqueous solution and 15 parts by weight of a crystalline cellulose powder having an average particle diameter of 0.03 mm was thoroughly blended and granulated into granules having diameters in the range from 0.05 to 0.10 mm. The granules were further admixed with 15 parts by weight of another crystalline cellulose powder having an average particle diameter of 1 mm and the blend was shaped by compression molding under a molding pressure of 500 kg/cm² into a form which was subjected to sintering at 1350° C. for 1 hour to give a sintered body. The physical properties of this sintered body were about the same as those of the sintered body prepared in Example 2.

EXAMPLE 4

Hydroxyapatite synthesized by the wet process was calcined at 900° C. for 1 hour and pulverized in a ball mill into a powder having an average particle diameter of 0.5 $\mu$m. The hydroxyapatite powder was admixed with 2% by weight of polyvinyl alcohol in an aqueous solution as a binder and granulated into granules having diameters in the range from 0.05 to 0.10 mm.

A blend composed of 100 parts by weight of the thus prepared granules, 15 parts by weight of a first crystalline cellulose powder having an average particle diameter of 0.05 mm and 15 parts by weight of a second crystalline cellulose powder having an average particle diameter of 0.2 mm was prepared and shaped into a form by compression molding under a molding pressure of 500 kg/cm². On the other hand, an aqueous slurry was formed by dispersing 100 parts by weight of the granules of hydroxyapatite and 15 parts by weight of the first crystalline cellulose powder having an average particle diameter of 0.05 mm in 150 parts by weight of water and the shaped form prepared by compression molding was coated with the aqueous slurry to form a coating layer of a uniform thickness followed by sintering at 1350° C. for 1 hour.

The thus obtained sintered body had a core-and-crust structure of which the core portion was a porous body of open pore structure having a porosity of 32% and a pore diameter distribution with two maxima at about 0.05 mm and at about 0.2 mm while the crust layer, which was also of an open pore structure, had a thickness of 0.5 mm and an average pore diameter of 0.05 mm. The bending strength of this sintered body of core-and-crust structure was 145.5 kg/cm² in the matrix of the core portion, i.e. the portion containing only the finer pores of 0.05 mm pore diameter on an average, while the bending strength of the body as a whole was 160.0 kg/cm².

The above prepared sintered body was cut into small pieces each having dimensions of 3 mm by 4 mm by 6 mm and including the crust layer on one surface and the pieces were used in the implantation test in just the same manner as in Example 2 using 5 rabbits as the test animals. The results of the dissective inspection of the rabbits after 2 months of raising were that the sintered body of hydroxyapatite had been partly absorbed with complete bonding between the neogenetic bone and the surface of the sintered body. No definite difference was found between the conditions on the surface of the crust layer and the cross section of the core portion.

EXAMPLE 5

Granules having diameters of about 1 to 2 mm prepared of a powdery blend composed of 100 parts by weight of the fine hydroxyapatite powder having an average particle diameter of 0.5 $\mu$m used in the preceding example, 2 parts by weight of polyvinyl alcohol and 15 parts by weight of a crystalline cellulose powder having an average particle diameter of 0.05 mm were subjected to sintering at 1350° C. for 1 hour.

Separately, an aqueous slurry was prepared by dispersing 100 parts by weight of the hydroxyapatite powder having an average particle diameter of 0.5 $\mu$m, 2 parts by weight of polyvinyl alcohol as an aqueous solution and 15 parts by weight of a crystalline cellulose powder having an average particle diameter of 0.05 mm in 150 parts by weight of water and the slurry was applied to the inner walls of a mold in a thickness of about 1 mm. The thus coated mold was then filled with a uniform blend of the sintered granules described above and 15 parts by weight of a crystalline cellulose powder having an average particle diameter of 1 mm and, after the coating layer formed of the slurry was completely dried, the filling body was taken out of the mold and sintered at 1350° C. for 1 hour. The thus obtained sintered body having a core-and-crust structure had a bending strength as high as that of the sintered body prepared in the preceding example and was equally useful as a prosthetic bone substitute member.

What is claimed is:

1. A sintered microporous hydroxyapatite material in a granular form composed of granules each having a diameter in the range from 0.1 to 2.0 mm and an open pore structure of micropores with a pore diameter distribution in the range from 0.01 to 0.10 mm and a porosity in the range from 20 to 50%.

2. The sintered microporous hydroxyapatite material in a granular form as claimed in claim 1 which is slurried with a physiological saline solution.

3. The sintered microporous hydroxyapatite material in a granular form as claimed in claim 2 wherein the amount of the saline solution is in the range from 50 to 200% of the granules of the sintered porous hydroxyapatite material by weight.

4. A sintered porous hydroxyapatite material in the form of a bone substitute member having an open pore structure provided with micropores having a pore diameter distribution in the range from 0.01 to 0.10 mm and pores having a pore diameter distribution in the range from 0.2 to 2.0 mm.

5. The sintered porous hydroxyapatite material in the form of a bone substitute member as claimed in claim 4 wherein the porosity of the material is in the range from 30 to 40%.

6. A sintered porous hydroxyapatite material in the form of a bone substitute member having a core-and-crust structure with an open pore structure which comprises a core partion provided with micropores having a pore diameter distribution in the range from 0.01 to 0.10 mm and pores having a pore diameter distribution in the range from 0.2 to 2.0 mm and a crust layer formed on the core portion provided with micropores having a pore diameter distribution in the range from 0.01 to 0.10 mm.

7. The sintered porous hydroxyapatite material in the form of a bone substitute member as claimed in claim 6 wherein the crust layer has a thickness in the range from 0.1 to 2.0 mm.

* * * * *